United States Patent [19]

Fiala

[11] Patent Number: 4,981,342
[45] Date of Patent: Jan. 1, 1991

[54] MULTIFOCAL BIREFRINGENT LENS SYSTEM

[75] Inventor: Werner J. Fiala, Vienna, Austria

[73] Assignee: Allergan Inc., Irvine, Calif.

[21] Appl. No.: 226,669

[22] Filed: Aug. 1, 1988

Related U.S. Application Data

[63] Continuation-in-part of Ser. No. 100,773, Sep. 24, 1987, abandoned.

[51] Int. Cl.$^5$ .......................... G02B 1/08; G02C 7/06
[52] U.S. Cl. .................................... 350/403; 350/379; 350/411; 351/161; 351/168
[58] Field of Search ............... 350/379, 403, 405, 411, 350/397; 351/161, 164, 168, 171

[56] References Cited

U.S. PATENT DOCUMENTS

| | | | |
|---|---|---|---|
| 3,520,592 | 7/1970 | Leib et al. | 350/379 |
| 3,551,027 | 12/1970 | Alexander III | 350/397 |
| 3,758,201 | 9/1973 | MacNeille | 350/403 |
| 4,446,305 | 5/1984 | Rogers et al. | 350/403 |
| 4,566,762 | 1/1986 | Kato | 350/411 |
| 4,643,534 | 2/1987 | Chun et al. | 350/403 |

FOREIGN PATENT DOCUMENTS

| | | | |
|---|---|---|---|
| 1236413 | 7/1960 | France . | |
| 231848 | 9/1925 | United Kingdom | 350/403 |
| 865361 | 4/1961 | United Kingdom | 350/411 |

OTHER PUBLICATIONS

Osipov, "Binary Polarizing Lenses," *Optical Technology*, vol. 40, No. 5, May 1973, pp. 277-279.
Eng et al., "Multiple Imagery With Birefringent Lenses," *Applied Optics*, vol. 8, No. 10, Oct. 1969, pp. 2117-2120.
*IBM Technical Disclosure Bulletin*, "Method For Aligning The Axes of a Birefringent Bifocal Lens System," vol. 27, No. 11, Apr. 1985, pp. 6674-6675.
Caulfield. "Digital Control of Focal Distances, " *Applied Optics*, vol. 6, No. 3, Mar. 1967, pp. 549-551.
Meyer-Arenot, *Introduction to Classical And Modern Optics*, 2nd ed., 1984, Prentice-Hall, London, pp. 336-339.
Born et al., *Principles Of Optics*, 6th ed., 1980, Pergamon Press, Oxford, pp. 684-707.
Fincham et al., *Optics*, 9th ed., 1980, Buttersworth, London, pp. 340-346.

Primary Examiner—Bruce Y. Arnold
Assistant Examiner—Martin Lerner
Attorney, Agent, or Firm—Dilworth & Barrese

[57] ABSTRACT

A multifocal birefringent lens system is described together with applications of the lens system such as ophthalmic lenses (including those of the intraocular, contact and spectacle type) and optical instruments and devices including photographic cameras, telescopes, microscopes, copiers, spectrographic instruments, etc.

20 Claims, 5 Drawing Sheets

MULTIFOCAL BIREFRINGENT LENS SYSTEM

This is a continuation-in-part of copending application Ser. No. 100,773 filed on Sept. 24, 1987, now abandoned.

BACKGROUND OF THE INVENTION

This invention relates to a multifocal non-achromatized or achromatized multicomponent optical lens system and, more particularly, to such a system wherein at least one of the lens components is a birefringent lens.

Birefringent lenses have been known for some time. U.K. Pat. No. 231,848 describes a birefringent lens which is used as a polarizer. Since a birefringent lens produces two orthogonally polarized light beams of different vergence, either a diaphragm or an isotropic lens is employed to eliminate one of the two polarized beams in order to provide a beam of one type of polarization only. U.S. Pat. No. 2,317,809 features a plano-convex birefringent lens cemented upon its convex side to a plano-concave isotropic lens. The assembly acts as a lens with positive power for light of one state of linear polarization and as a parallel plate with zero optical power for light of the other, orthogonal state of polarization. The lens assembly is integrated in a finder for photographic In U.K. Pat. No. 865,361, a prismatic birefringent lens is combined with an isotropic cover lens in such a way that the two powers of the combination of lenses are equidistant from the target power. The lens system is incorporated in optical apparatus for testing the human eye. The apparatus separates the two images formed by the o- and e-rays so that two images of different degrees of acuteness can be viewed simultaneously and side-by-side during eye examination. U.S. Pat. No. 3,211,048 makes mention of plano-convex/plano-concave doublet lens assemblies made of identical birefringent materials. In the assemblies, one of the two birefringent lenses may be replaced by an isotropic lens with a plane surface. The assemblies work in concert with a dispersive device, e.g., a prism, and a polarizer in a spectrometer. U.S. Pat. No. 3,432,238 also discloses doublets of plano-concave/plano-convex birefringent lenses for the production of phase shifts of incident polarized light. The resultant interference patterns are utilized in a spectrometric apparatus.

Since a birefringent lens has one power associated with one plane of linear polarization and another power with the other, orthogonal plane of polarization, means which are able to rotate the plane of polarization can be used to select one of the two powers if the incoming light is linearly polarized. U.S. Pat. No. 3,410,624 uses electro-optic control means (a Kerr cell) together with birefringent lenses and prisms. It is disclosed in this patent that m systems comprising each a lens and an electro-optic cell can produce 2m focal points. A similar assembly of n electro-optic cells and n birefringent lenses is disclosed in French Pat. No. 1552198. U.S. Pat. No. 3,520,592 and Eng. et al., "Multiple Imagery with Birefringent Lenses", *Applied Optics*, Vol. 8, No. 10, pp. 2117–2120 (October, 1969) each disclose an optical focusing system using one or more birefringent lenses, each lens combined with a control device for the polarization plane of light U.S. Pat. No. 3,563,632 discloses a digital optical focal length modulator in which an assembly of aligned successive stages, each possessing a Kerr cell and a birefringent lens of progressive curvature, is immersed in a common electrolytic tank. The lenses are shaped such that the temperature-dependence of the refractive index of the electrolyte is compensated. U.S. Pat. No. 3,565,510 discloses the use of two birefringent lenses per Kerr cell in a system analogous to that mentioned in aforesaid U.S. Pat. No. 3,563,632. Osipov, "Binary polarizing lenses", *Optical Technology*, Vol. 40, No. 5, pp. 277–279 (May, 1973) describes a binary polarizing lens consisting of a plano-convex/plano-concave birefringent lens system. This lens system may be combined with an isotropic lens in order to produce a parallel reference beam and a focused signal beam, the beams being polarized orthogonally, for use in laser systems. U.S. Pat. No. 3,758,201 discloses a plano-convex/plano-concave birefringent doublet lens in combination with an isotropic variable power lens system. The system is used in eye examination. U.S. Pat. No. 3,990,798 discloses a plano-convex/plano-concave birefringent lens doublet for use as, or in, an eyepiece of a microscope in order to produce the images of objects within different object planes in a single image plane. Plano-convex/plano-concave doublet lenses made of birefringent material are also disclosed in U.S. Pat. No. 4,566,762 describing a dual focus system in which the images of differently distant objects exhibit identical magnification. U.S. Pat. No. 4,575,849 discloses plano-convex/plano-concave birefringent lenses which are used as phase-plates in an optical filter-polarizer combination.

It appears from the foregoing that birefringent lenses have been used primarily in plano-convex/plano-concave lens assemblies. Such an assembly is combined in one instance, i.e., in Osipov, with an isotropic lens in order to produce a parallel beam of polarized light. A combination of a prismatic birefringent and a prismatic isotropic lens is used in U.K. Pat. No. 865,361, supra, to produce two side by side images of one object for the purpose of eye examination. Furthermore, assemblies of systems, each system incorporating a birefringent lens and a control means for the orientation of the polarization plane have been suggested as variable focal distance systems in various patents.

In the above-mentioned prior disclosures inorganic crystals such as quartz and calcite are mentioned as birefringent lens materials. Birefringence can also be a property of some kinds of organic polymers. Thus, for example, U.S. Pat. Nos. 4,384,107; 4,393,194; 4,933,196; 4,433,132; 4,446,305; 4,461,886; 4,461,887; 4,503,248; 4,520,189; 4,521,588; 4,525,413; 4,575,547; 4,608,429; and, 4,628,125 describe polymers which exhibit high birefringence and simulate the optical properties of uniaxial crystals. Such birefringent polymers are proposed for use with isotropic layers in multilayer light transmitting and polarizing devices.

The fact that many polymers can be birefringent by, e.g., applying stress is known. The entire field of photoelasticity and stress analysis by means of polarized light is based on this phenomenon. It is also known that by stretching a polymer beyond its elastic range, birefringence can be imparted to the polymer irreversibly. Mention of this is made, e.g., in U.S. Pat. No. 3,522,985.

Ophthalmic lenses having multiple foci and, in particular, contact lenses possessing this property are known, e.g., U.S. Pat. Nos. 3,794,414; 4,162,122; 4,210,391; 4,340,283; 4,338,005; 4,637,697; 4,641,934; 4,642,112; and, 4,655,565. It is common to these lenses that the optical media employed in their fabrication are isotropic. The simultaneous multipower features are achieved by providing the lens with appropriate geometrical parameters.

SUMMARY OF THE INVENTION

It is an object of the present invention to provide a multifocal, e.g., bifocal, trifocal, quadrafocal, etc., non-achromatized or achromatized birefringent lens system in which at least two foci are selected in total independence of one another.

It is another object of the invention to provide a multifocal non-achromatized or achromatized birefringent lens system exhibiting a minimum of unwanted foci or powers.

It is another object of the present invention to provide a non-achromatized or achromatized multifocal birefringent lens system which is superior with respect to image brightness, chromatic behavior and freedom of choice of powers compared to other known types of multifocal lens systems.

It is a particular object of the present invention to provide a non-achromatized or achromatized birefringent lens system fabricated in whole or in part from optical grade polymers.

It is another particular object of the invention to combine a non-achromatized or achromatized birefringent lens system with one or more light polarizer means and, optionally, one or more polarizing filters, to permit a selection of powers or combinations of powers from among a multiplicity of available powers.

It is still another object of the invention to provide a multifocal non-achromatized or achromatized birefringent lens system in which at least one lens surface is given a shape in independence of the physical parameters of the media employed in the fabrication of the lens components and in independence of the preselected foci.

It is a further particular object of the invention to provide a birefringent lens system exhibiting any desired degree of chromatic aberration in at least one focus of the preselected foci.

It is yet another object of the invention to provide ophthalmic lenses, in particular, spectacle lenses, contact lenses and intraocular lenses, based on the non-achromatized or achromatized birefringent lens system herein.

Other objects of the invention include incorporating the birefringent lens system herein as well as other optical devices incorporating such a lens system, e.g., ophthalmic diagnostic instruments, cameras, telescopes and field glasses, microscopes, copiers, optical benches, spectrographic instruments, etc.

In accordance with this invention, there is provided a multifocal non-achromatized birefringent lens system which comprises:

(a) a first lens component which is a birefringent lens component; and, (b) a second lens component adjacent to said first lens component, the curvatures of the opposed surfaces of the first and second lens components being substantially identical or complementary, said second lens component being (i) a birefringent lens component possessing an optic axis of different orientation than that of the optic axis of birefringent lens component (a) or
  (ii) a birefringent lens component wherein both indices of refraction differ from those of birefringent lens component (a) or
  (iii) a birefringent lens component wherein the refraction index for the ordinary light waves is the same as that for birefringent lens component (a) but wherein the refractive index for the extraordinary light waves differs from that for birefringent lens component (a) or
  (iv) a birefringent lens component wherein the refractive index for the extraordinary light waves is the same as that for birefringent lens component (a) but wherein the refractive index for the ordinary light waves differs from that for birefringent lens component (a) or
  (v) an isotropic lens component, provided, that for light which is incident in parallel with the lens axis, said lens system possesses simultaneously at least two foci each of which is positioned at any preselected positive or negative focal distance on the axis of the lens system and further provided that any one surface of either the first or second lens component is given a curvature in independence of said preselected foci.

Further, in accordance with this invention, there is also provided a multifocal birefringent lens system which is achromatic in at least one focus or which exhibits a predetermined amount of chromatic aberration in at least one focus which comprises:

(a) a first lens component which is a birefringent lens component possessing an optic axis which is substantially perpendicular to the lens axis; and, (b) a second lens component adjacent to said first lens component, said second lens component being (i) a birefringent lens component possessing an optic axis of different orientation than that of the optic axis of birefringent lens component (a) or
  (ii) a birefringent lens component wherein both indices of refraction differ from those of birefringent lens component (a) or
  (iii) a birefringent lens component wherein the refraction index for the ordinary light waves is the same as that for birefringent lens component (a) but wherein the refractive index for the extraordinary light waves differs from that for birefringent lens component (a) or
  (iv) a birefringent lens component wherein the refractive index for the extraordinary light waves is the same as that for birefringent lens component (a) but wherein the refractive index for the ordinary light waves differs from that for birefringent lens component (a) or
  (v) an isotropic lens component, provided, that for light which is incident in parallel with the lens axis, said lens system simultaneously possesses at least two foci each of which is positioned at any preselected positive or negative focal distance on the axis of the lens system and further provided that at least the focal distance of one of the two foci is essentially equal for of at least two different wavelengths of the focused light.

The term "adjacent" used in reference to the relative positioning of the first and second lens components of the birefringent lens system herein is intended to include the case where such components are in direct mutual contact for substantially their entire opposed surfaces, i.e., "compound lens" or "lens in compound" as defined, below and the case where such opposed surfaces are separated a short distance along their common axis, typically a distance of a few millimeters or less.

The expression "substantially identical or complementary" as applied to the curvatures of the opposed surfaces of the first and second lens components of the multifocal non-achromatized birefringent lens system herein shall be understood to mean that were such surfaces to be placed in contact with each other, they would meet at every point along their mutual interface. Thus, e.g., in the case of substantially identical curvatures, such curvatures would be flat or planar, i.e., the surfaces would have an infinite radius of curvature, and in the case of complementary curvatures, such surfaces would be represented, e.g., by matching concave and convex surfaces.

The expressions "compound lens" or "lenses in compound" shall be understood herein to refer to a lens system comprising at least two lens components, two opposed lens surfaces of adjacent lens components being substantially identical or complimentary so that the two lens component can be cemented together along their opposed surfaces, e.g., in a plano-concave/-plano-convex lens systems. These expressions also apply to a lens system wherein the opposed lens surfaces are separated by a certain distance in order to accommodate one or more optical devices other than a lens, e.g., a polarizing means.

The expression "lenses in contact" shall be understood herein to refer to a lens system comprising at least two lens components which lens system satisfies essentially the requirement that the optical power of the lens system is equal to the sum of the optical powers of the lens components.

The term "non-achromatized" shall be understood to refer to a lens or lens systems which exhibits one or more powers which still depend on the wavelength of the focused (i.e., used) light due to the dispersive behavior of the birefringent and/or isotropic optical media employed in the fabrication of the lens or lens system.

The term "achromatized" shall be understood to refer to a lens system which exhibits one or more powers at least one of which exhibits a dioptric value which is constant for at least two different wavelengths of the focused (i.e., used) light.

The multifocal non-achromatized and achromatized birefringent lens systems of the present invention includes numerous permutations and combinations of a birefringent lens component with at least one other birefringent lens component and/or at least one isotropic lens component as set forth above, provided that in such a system, at least two of the resulting foci, or powers are preselectable, that such foci lie along the same lens axis for light which is incident in parallel with the lens axis and that any one curvature of either the first or second lens component is chosen in independence of the preselected foci. Within the restraints imposed by these requirements, it is possible to provide any of a very wide variety of multifocal optical designs to meet any number of practical requirements. So, for example, the invention includes lens systems in which: a single birefringent lens component is combined with one or more isotropic lens components to provide a compound lens or train of lenses; one birefringent lens component is combined with at least one other birefringent lens component, either as a compound lens or as a train of such lenses, optionally with one or more isotropic lens components, and so forth. In addition, and as will be explained, infra, any of the multifocal birefringent lens systems of this invention can be utilized in conjunction with other polarizing media or polarizing filters positioned between one or more adjacent pairs of birefringent lens components and/or in front or behind the lens system, thereby permitting selection of one or more powers from amongst a multiplicity of available powers.

The latitude in choice of optical powers made possible by the multifocal birefringent lens system of this invention can be exploited to advantage in any number of applications, notably, in the design of ophthalmic bifocal lenses where even relatively large differences in power can be easily achieved with relatively thin lenses, and in various types of optical instruments and apparatus including telescopes, binoculars, video and photographic camera lenses, microscopes, copiers, optical benches, spectrographic instruments, etc.

DESCRIPTION OF THE PREFERRED EMBODIMENTS

A. Multifocal Non-achromatized Birefringent Lens Systems

All known birefringent lens systems possess an optic axis (i.e., the axis within the interior of the crystalline birefringent medium) which is perpendicular to the lens axis. Thus, a birefringent lens system exhibits two particular indices of refraction, $n_o$ (for the ordinary waves, or rays) and $n_e$ (for the extraordinary waves, or rays), but only for the particular case where the e-rays transverse the birefringent lens in a direction which is perpendicular, i.e., orthogonal, to the optic axis. For all other directions, the e-rays possess an effective index of refraction $n_{e,eff}$ which has a value between $n_o$ and $n_e$. In such a case, it is not possible to predict with any exactness the optical performance or behavior of the birefringent lens system for the e-rays.

For this reason it may be desirable to employ a bifocal lens system exhibiting two independently selected powers (or foci) with the additional feature that the e-rays transverse the birefringent lens in a direction which is exclusively perpendicular to the optic axis. The case where all e-rays transverse the birefringent lens in an orthogonal direction to the optic axis will be referred to as the "perfect geometry" embodiment of the birefringent lens system herein.

Figure 1:
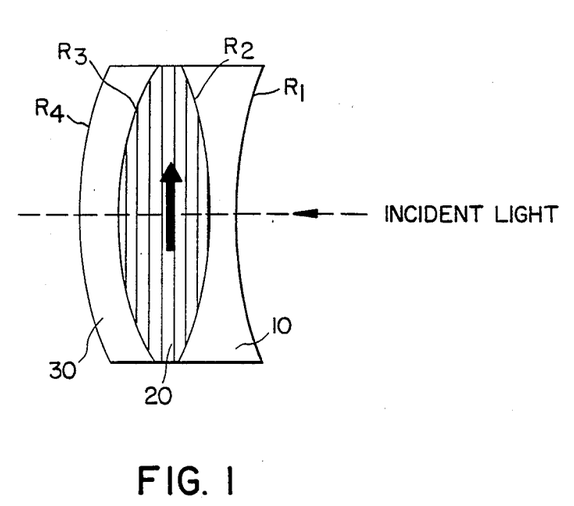
FIG. 1 is a schematic illustration of a birefringent lens system in accordance with the invention exhibiting a "perfect geometry"

FIG. 1 illustrates one embodiment of a birefringent lens system of perfect geometry possessing isotropic lens component 10 possessing spherical surfaces $R_1$ and $R_2$ and isotropic lens component 30 possessing spherical surfaces $R_3$ and $R_4$ in front of, and in back of, birefringent lens component 20 possessing complementary spherical surfaces $R_2$ and $R_3$ with the solid arrow indicating its optic axis (as will be the case in all subsequent figures herein). Assigning the preselected powers (which also define the corresponding foci) $D_a$ and $D_b$ to the lens system, the following restrictions apply to a bifocal lens system of perfect geometry:

$$D_{34} + D_o + D_{12} = D_a \quad (1a)$$

$$D_{34} + D_e + D_{12} = D_b \quad (1b)$$

and the "perfect geometry" restriction:

$$(n_e - 1) \times \frac{1}{R_2} = -D_{12} \quad (2)$$

where $D_{12}$ and $D_{34}$ are the powers of the front and back isotropic lens components respectively, and $D_o$ and $D_e$ are the powers of the birefringent lens component for the o-rays and e-rays.

For this perfect geometry embodiment, the relation $$\frac{D_o}{n_o - 1} = \frac{D_e}{n_e - 1} \quad (3)$$

applies, or $$D_e = m \cdot D_o \quad (4)$$

where $$m = \frac{n_e - 1}{n_o - 1} \quad (5)$$

With this, the perfect geometry bifocal lens system of FIG. 1 is described by:

$$D_o = \frac{D_a - D_b}{n_o - n_e} \times (n_o - 1) \quad (6a)$$

$$D_e = \frac{D_a - D_b}{n_o - n_e} \times (n_e - 1) \quad (6b)$$

$$D_{34} = D_a - D_o - D_{12} \quad (7)$$

If, e.g., the radius $R_3$ is preselected, then $R_2$ can be calculated in view of equations (6a) or (6b). Then, with the calculated radius $R_2$ and equation (2), the radius $R_1$ is to be determined, and with preselected radius $R_3$ and equation (7), $R_4$ can be calculated. In principle, any one of the four radii can be preselected.

For the more general embodiment of a non-perfect geometry birefringent lens system, the e-waves transverse the birefringent lens in a direction which is not necessarily perpendicular to the optic axis. The e-rays thus possess individual effective indices of refraction $n_{e,eff}$ with values between $n_e$ and $n_o$. As neither the effective indices $n_{e,eff}$ nor the paths of the e-rays within the birefringent lens are known beforehand, the paths and the effective indices $n_{e,eff}$ being mutually dependent, the actual performance of a lens system incorporating a birefringent lens cannot be judged on the values of $n_e$ and the lens geometry directly.

A reasonable calculation of the performance of birefringent lenses has to be based on a detailed ray tracing of light rays through such a lens. Such a ray tracing involves the determination of the spatial components of the light propagation vectors before and after an arbitrarily oriented interface between an isotropic and a birefringent medium. For a given choice of orientation of the optic axis of the birefringent medium, this determination involves Huygens' construction, i.e., the general case of a construction of a tangent plane on a elliptical toroid; see, e.g., J. Strong: "Concepts of Classical Optics", p. 138, W. H. Freeman and Company (1958). On the basis of such ray tracing calculations, which, of course, can also be prepared for the o-rays, practically all interesting lens performance data such as lens powers, image acuity, chromatic and spherical aberration can be evaluated. The inclusion of the Fresnel formulae for the transmitted amplitude of light crossing the boundary between two optical media also allows for the determination of the transmitted intensities of a multilayer lens.

Examples of non-perfect geometry birefringent lens systems in accordance with this invention will now be given in conjunction with the accompanying FIGS. 2-5. In these examples, the following definitions are used:

| Value | Definition |
|---|---|
| DVO | The back vertex power for o-rays from usual back vertex power calculations. |
| DVE | The back vertex power for e-rays from usual back vertex power calculations. |
| DO | The back vertex power for o-rays from ray tracing calculations. |
| DE | The back vertex power for e-rays from ray tracing calculations. |
| ACM | The "acuity measure", i.e., the ratio between the area of the minimum focal spot and the area (i.e., cross section) of the lens. |
| PTR | The percentage of average transmitted intensity of the incident intensity associated with a power. |
| $n_o$ | The index of refraction of the birefringent lens for the o-rays. |
| $n_e$ | The index of refraction of the birefringent lens component for the e-rays in the case where the e-rays are perpendicular to the optic axis. |
| $n_{12}$ | The index of refraction of the isotropic lens component possessing the radii $R_1$ and $R_2$. |
| $n_{34}$ | The index of refraction of the isotropic lens component possessing the radii $R_3$ and $R_4$. |
| gamma | The angle between the optic axis and the lens axis. |
| $alpha_r$ | The angle between the incident light rays and the lens axis. |
| $alpha_p$ | The angle between the plane formed by the incident light rays and the lens axis and the plane formed by the optic axis of the birefringent lens component and the lens axis. |
| $R_1, R_2, R_3$ and $R_4$ | The radii of the spherical lens surfaces of the lens system of FIGS. 2-5. |
| d | The diameter of the lens system. |
| $C_{12}, C_{23}$ and $C_{34}$ | The lens center thicknesses of the lens systems of FIGS. 2-5. |
| DF | The inverse distance (in diopters) between the focal spot and the center of the back surface of the lens system. |
| $D_{pr}$ | The prismatic power in prismatic diopters (1 prismatic diopter = 1 cm deviation per meter). |

Figure 2:
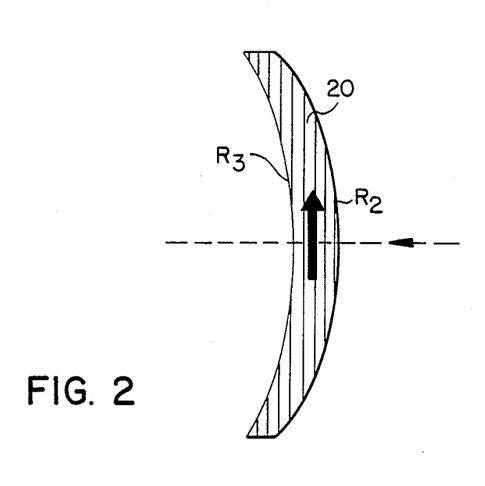
FIG. 2 is a schematic illustration of a birefringent lens component which is to be incorporated in a lens system of the present invention.

The design specifications of birefringent lens component 20 of FIG. 2 are as follows:
Front Surface Radius: $R_2 = 7.5$ mm Back Surface Radius: $R_3 = 7.8$ mm
Center Thickness: $C_{23} = 0.05$ mm
Lens System Diameter: $d = 6$ mm
Orientation of Optic Axis: gamma $= 90°$
Indices of Refraction: $n_o = 1.443$; $n_e = 1.8$
Direction of Incident Light: $alpha_r = 0°$

TABLE 1

| Calculated Values for the O-Rays of the Birefringent Lens Component of FIG. 2 | | | |
|---|---|---|---|
| DVO | DO | ACM | PTR |
| 2.39 | 2.84 | $4.8 \times 10^{-3}$ | 93% |

| Calculated Values for the E-Rays of the Birefringent Lens Component of FIG. 2 | | | |
|---|---|---|---|
| DVE | DE | ACM | PTR |
| 4.42 | 5.11 | $2.85 \times 10^{-3}$ | 79% |

The foregoing data show that the actual back vertex powers DO and DE are larger than the corresponding values of DVO and DVE. This is due to the non-zero aperture of the incoming bundle of light rays. It can actually be shown that for incident light of zero aperture, DO and DVO agree completely and DE and DVE nearly coincide. For the case of on-axis incident light, the two focal spots are located exactly on the lens axis. It is to be noted that the image acuity of the e-rays is excellent by comparison with the acuity of the o-rays. Transmission losses for e-rays are higher than for the o-rays because the e-rays deviate to a larger extent than the o-rays.

Figure 3A:
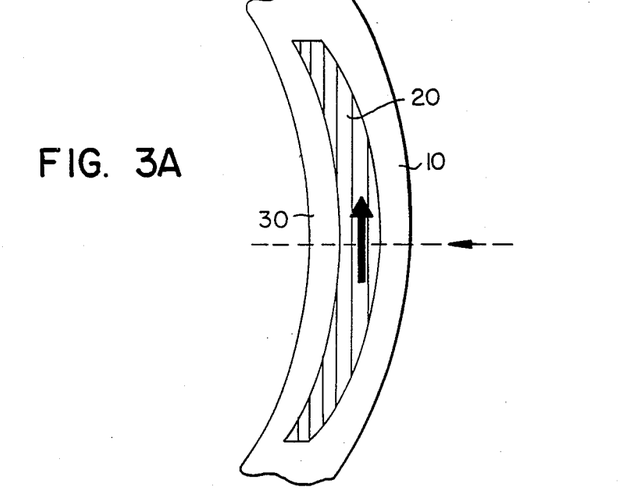
FIGS. 3A, 3B, 4 and 5 are schematic illustrations of various other embodiments of birefringent lens systems in accordance with the invention.
Figure 3B:
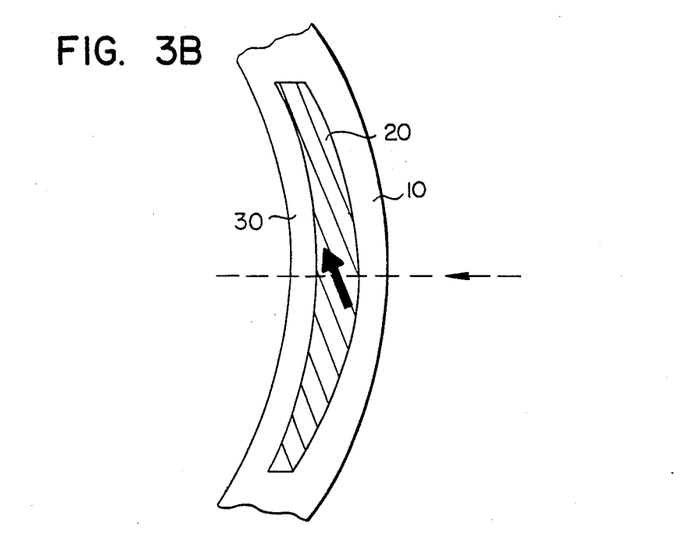

In the birefringent lens system of FIGS. 3A and 3B, birefringent lens component 20 of FIG. 2 is combined with isotropic lens components 10 and 30. The only difference between these two lens systems is the orientation of the optic axis birefringent lens component 30 which is essentially perpendicular to the lens axis in FIG. 3A and tilted approximately 60° relative to the lens axis in FIG. 3B. The lens parameters for both lens systems are chosen such that the lens systems are practically afocal for the ordinary rays (i.e., they exhibit zero power) and that they exhibit a positive power for the e-rays. These parameters are as follows:

| Radii | $R_1 = 7.85$ mm |
|---|---|
| | $R_2 = 7.5$ mm |
| | $R_3 = 7.8$ mm |
| | $R_4 = 7.8$ mm |
| Center Thicknesses | $C_{12} = 0.04$ mm |
| | $C_{23} = 0.05$ mm |
| | $C_{34} = 0.03$ mm |
| Lens System Diameter | $d = 6$ mm |
| Lens Media | $n_{12} = 1.443$ |
| | $n_o = 1.443$; $n_e = 1.8$ |
| | $n_{34} = 1.443$ |
| Orietion of optic Axis | gamma $= 90°$ |
| Direction of Incident Light | $alpha_r = 0°$ |

TABLE 2

| Calculated Values for the O-Rays of Birefringent Lens Component of FIG. 3A | | | |
|---|---|---|---|
| DVO | DO | ACM | PTR |
| $-.10$ | $-.10$ | $.75 \times 10^{-3}$ | 93% |

| Calculated Values for the E-Rays of Birefringent Lens Component of FIG. 3A | | | |
|---|---|---|---|
| DVE | DE | ACM | PTR |
| 1.93 | 2.11 | $7.5 \times 10^{-3}$ | 85% |

Again, for all incident rays parallel to the lens axis, the two focal spots are located exactly on the lens axis. The transmitted intensity of the e-rays has increased as compared to the case of the single birefringent lens (FIG. 2) but the acuity has deteriorated slightly.

Still referring to the lens system of FIG. 3A, the performance of the system for off-axis incident light is presented. The discussion of the calculations set forth in Tables 3 and 4, infra, is restricted to the e-rays since the o-rays behave in a manner which can be determined from known isotropic lenses.

First, data for the case of a bundle of incident light rays where the angle between the plane of incidence and the optic axis of the birefringent lens component is zero are presented below in Table 3:

TABLE 3

| Direction of Incident Light: $alpha_r = 30°$; $alpha_p = 0°$ | | | | |
|---|---|---|---|---|
| DVE* | DF | ACM | PTR | $D_{pr}$ |
| 1.93 | 1.93 | $98 \times 10^{-3}$ | 89% | 0.75 |

*Calculated for on-axis incident light

From these data, it will be appreciated that a birefringent lens system in accordance with this invention exhibits an effective power DF which is practically identical with the power DVE for on-axis incident light. From a lens design point of view, such a characteristic can be advantageous, for example, in the case of an ophthalmic lens, and in particular, a contact lens, where it can be desirable to maintain the same effective power regardless of the angle of incident light relative to the lens axis even if there may be some loss of image acuity.

Second, the performance data of this lens system for off-axis incident light rays where the optic axis is perpendicular to the plane of the incident light are presented in Table 4 as follows:

TABLE 4

| Direction of Incoming Incident Light: $alpha_r = 30°$; $alpha_p = 90°$ | | | | |
|---|---|---|---|---|
| DVE* | DF | ACM—e-rays | PTR | $D_{pr}$ |
| 1.93 | 2.24 | $35 \times 10^{-3}$ | 89% | 0.74 |

*Calculated for on-axis incident light

For this type of incident light, comparative analyses show that the birefringent lens system of this invention performs very much like an isotropic lens system of identical power DVE. The practical consequence of this for, say, the design of a contact lens is that standard optic relationships and properties remain essentially true for the present birefringent lens system for this type of incident light.

The combined data of Tables 3 and 4 indicate that in the case of a bifocal contact lens, the reading addition is preferably provided by the e-rays and the distance addition is preferably provided by the o-rays. These same data further indicate that the optic axis of a bifocal contact lens should be oriented in a direction which is substantially vertical where the visual field is being interpreted horizontally, e.g., from left to right. Conversely, where the visual field is being viewed primarily in a vertical direction, the data of FIGS. 3 and 4 indicate that the direction of the optic axis of the bifocal contact lens should be substantially horizontal.

As pointed out, supra, only one birefringent lens component and one isotropic lens component are required in order to provide two independently preselected powers. However, it can be advantageous to provide a three or more lens-component system for particular applications. One such lens system contemplated by this invention and schematically illustrated in FIG. 3A includes a scleral contact lens in which birefringent lens component 20, the diameter of which corresponds, to the maximum diameter of the pupil, is embedded or encased in an isotropic lens component whose diameter corresponds to the diameter of the sclera. The isotropic lens component in front of and in back of the birefringent lens component, 10 and 30, respectively, can be regarded as the two isotropic lens components of the overall lens system. The various components can be fabricated from the same or different optical media. For example, a birefringent polymer such as any of those described in the above-referenced prior patents or an oriented polymer, e.g., polymethyl methacrylate which has been stretched, can be combined with any known isotropic contact lens media such as hydromethyl methacrylate polymer or (unstretched) polymethyl methacrylate to provide a bifocal contact lens in accordance with this invention.

Figure 4:
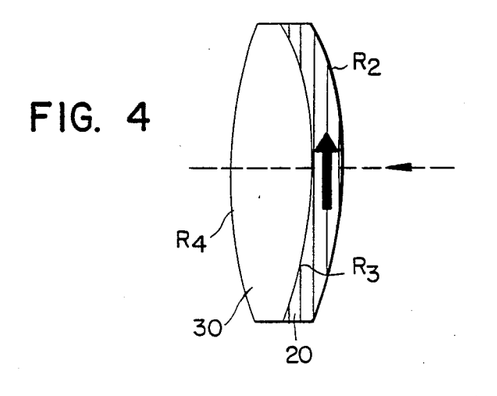

FIG. 4 illustrates another birefringent lens system in accordance with this invention possessing the following design parameters for birefringent lens component 20 and isotropic lens component 30:

| Radii | $R_2 = 38$ mm |
| --- | --- |
|  | $R_3 = 50$ mm |
|  | $R_4 = -50$ mm |
| Center Thicknesses | $C_{23} = 0.2$ mm |
|  | $C_{34} = 1.0$ mm |
| Lens System Diameter | $d = 6$ mm |
| Lens Media | $n_o = 1.443; n_e = 1.8$ |
|  | $n_{34} = 1.443$ |
| Orientation of Optic Axis | gamma = 90° |
| Direction of Incident Light | alpha$_r$ = 0° |

TABLE 5

| Calculated Values for the O-Rays of the Birefringent Lens Component of FIG. 4 | | | |
| --- | --- | --- | --- |
| DVO | DO | ACM | PTR |
| 20.63 | 20.77 | $.007 \times 10^{-3}$ | 93% |
| Calculated Values for the E-Rays of the Birefringent Lens Component of FIG. 4 | | | |
| DVE | DE | ACM | PTR |
| 22.96 | 23.03 | $.008 \times 10^{-3}$ | 88% |

The foregoing results indicate that birefringent lens systems of the present invention can be used as a bifocal intraocular lens.

As shown in FIG. 3B, birefringent lens systems in accordance with the invention are bifocal for orientations of the optic axis other than perpendicular to the lens axis also.

TABLE 6

| Calculated Values for the O-Rays of the Birefringent Lens Component of FIG. 3B | | | |
| --- | --- | --- | --- |
| DVO | DO | ACM | PTR |

TABLE 6-continued

| -.10 | -.10 | $.75 \times 10^{-3}$ | 93% |
| --- | --- | --- | --- |
| Calculated Values for the E-Rays of the Birefringent Lens Component of FIG. 3B | | | |
| DVE** | DE | ACM | PTR |
| 1.93 | 1.80 | $68 \times 10^{-3}$ | 85% |

**Calculated for gamma = 90°

As can be seen from the foregoing calculations, the power associated with the e-rays has decreased. This is due to the fact that the effective indices of refraction $n_{e,eff}$ are smaller than $n_e$. Image quality for the e-rays is poorer than for the case of gamma=90°. Therefore, only in a few instances it will be suitable to use other angles between the optic and the lens axes than gamma=90°.

However, for at most only small deviations of gamma from 90°, lens performance can be satisfactory. Therefore, it is within the scope of the invention to bend a sheet of birefringent polymer the optic axis of which lies within the sheet's plane so that it exhibits a cylindrical surface, the axis of the cylinder being perpendicular to the then circular optic axes. The cylinder radius can, e.g., be given a value which corresponds to one of the radii of the birefringent lens. Analysis of such a lens shows that it will perform almost identically to a lens which exhibits an optic axis perpendicular to the lens axis throughout the lens. As is evident, the approximation gets closer with increasing cylinder radius.

Figure 5:
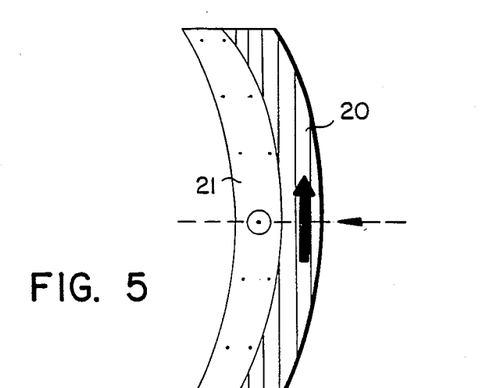

In the previously described embodiments, a birefringent lens component was combined with one or two isotropic lens components in order to provide two different powers the magnitude of which can be chosen in complete independence of one another even at a remaining free geometrical parameter for the compound lens system. In the case of, e.g., a contact lens, this free parameter is available for the design of the back surface curvature of the lens system. This effect can, in general, also be achieved by combining two birefringent lens components. In order to produce two powers only, the angle between the optic axes of the two birefringent lenses must be 90° so that the o-rays in the first birefringent lens will be the e-rays in the second and vice-versa. This configuration, which can be referred to as a "crossed birefringent" lens system, is illustrated in FIG. 5.

The design parameters of the lens system of FIG. 5 consisting of birefringent lens components 20 and 21 are as follows:

| Front surface radius | 7.9 mm |
| --- | --- |
| Intermediate surface radius | 7.5 mm |
| Back surface radius | 7.8 mm |
| Center Thickness, first lens | 0.06 mm |
| Center Thickness, second lens | 0.06 mm |
| Lens System Diameter | 6.0 mm |
| Optical Media, | |
| first lens | $n_o = 1.443; n_e = 1.8$ |
| second lens | $n_o = 1.443; n_e = 1.8$ |
| Orientation of optic axes | gamma$_1$ = gamma$_2$ = 90° |
| Angle between optic axes | 90° |
| Direction of incident light | alpha$_r$ = 0° |

In the calculation set forth in Table 7, the following values have the definitions given herein:

| Value | Definition |
| --- | --- |
| DOE | The power associated with the o-rays in the first, and the e-rays in the second, lens. |
| DEO | The power associated with the e-rays in the first, and the o-rays in the second, lens. |
| DVOE and DVEO | The corresponding powers obtained from conventional back vertex power calculations. |

TABLE 7

Calculated Values for the Birefringent Lens System of FIG. 5

| DVOE | DOE | DVEO | DEO |
| --- | --- | --- | --- |
| 1.60 | 1.84 | −2.66 | −2.82 |

Image acuity provided by the lens system of FIG. 5 is of the same order of magnitude for on-axis incident light as in the case of an isotropic-birefringent lens system, e.g., that of FIG. 3A.

Crossed birefringent configurations are capable of producing large power differences for the two orthogonally polarized emerging light waves, even with very thin lenses. Accordingly, such configurations can be utilized for contact lenses.

The foregoing embodiments indicate that the birefringent lens system according to this invention can be advantageously used as an ophthalmic contact lens or as an intraocular lens where at least two different powers, at least one for distance vision and at least one for reading, are required.

Figure 9A:
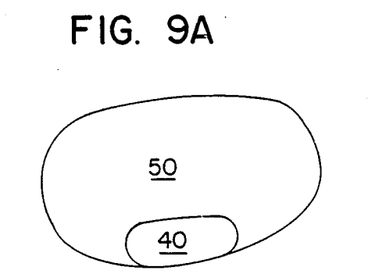
Figure 9B:
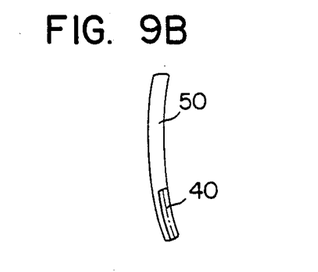

Embodiments of the present birefringent lens systems can also serve as, or be integrated in, ophthalmic spectacle lenses. A preferred embodiment of such a lens is illustrated in FIGS. 9A and 9B wherein 40 represents the bifocal birefringent lens portion, e.g., with a birefringent-isotropic lens system for reading and distance vision, and 50 represents the monofocal lens portion for distance vision fabricated from convention isotropic media. In the spectacle lens of FIGS. 9A and 9B, the power corresponding to the o-rays of lens portion 40 is identical with the power of lens portion 50. Advantageously the isotropic medium used in portions 40 and 50 is the same throughout, e.g., polyacrylate, and the birefringent medium from which the birefringent lens component of portion 40 is constructed is stretched polyacrylate. For reading, the on-axis incident light rays are primarily used, i.e., eye movement is such as to maintain a straight line (namely, the lens axis) between the text being read and the pupil. Such an eye movement does not usually involve a head movement. Typical reading distance in front of the eye is about 40 cm and printed texts typically extend 20 cm from left to right. Consequently, the eye's lens axis sweeps out an angle of approximately 30° during reading horizontally printed texts. The lens of an eye glass is typically 12 mm in front of the cornea. Therefore, the zone of a spectacle lens which provides the reading power does not have to measure more than approximately 1 cm across in the horizontal direction. In any case, the reading addition zone need not be any broader than 2 cm. In the vertical direction, the reading addition zone may measure only 1 to 1.5 cm. The zone can advantageously be positioned at the bottom of the spectacle lens as illustrated in the embodiment of FIGS. 9A and 9B.

The use of a birefringent bifocal lens system within such a reading addition zone offers decisive advantages over conventional two-zone bifocal spectacle lenses where both zones are each monofocal. Although the above considerations for the required dimensions of a reading addition zone would also apply for conventional bifocal spectacle lenses, such lenses usually exhibit considerably larger reading addition zones. This is mainly due to the fact that conventional spectacle lenses with such a small zone of higher power would be cosmetically unappealing.

Birefringent lens systems, by comparison, have the appearance of monofocal lenses which means that the reading addition zone is not discernible from the distance vision zone, in particular, if as previously noted the birefringent lens exhibits an index of refraction $n_o$ which is identical with the index of refraction used in the distance vision lens. A rather small reading addition zone, by contrast, can provide rather large reading powers at modest lens thicknesses which can reduce the overall weight of the spectacle lenses. Finally, it is to be noted that the birefringent lens system herein provides the required powers for both reading and distance vision simultaneously. Therefore, the field of view extends over the entire spectacle lens area, which is important in the case where distance vision is required in a downward direction or, e.g., when distant objects are viewed by someone in a reclined position. With present bifocal spectacles, one has to bend the head considerably forward in order to be able to look over the reading addition zone.

As mentioned, supra, the two powers of a birefringent lens system are produced by two orthogonally polarized light waves. If, by way of example, the distance vision power is associated with a light wave in a vertical polarization plane and the reading power with a light wave in a horizontal polarization plane, sunglasses incorporating polarizing filters can be advantageously employed to select exclusively every one of the two available powers in dependence of the direction of gaze. Such sunglasses would have, by way of this example, to incorporate a polarizing filter which produces vertically polarized light in the larger zone for distance vision and a polarizing filter which produces horizontally polarized light in the smaller zone for reading. Distance vision and reading zone distribution will correspond to the distribution apparent from FIG. 9A. With such sunglasses, the out-of-focus light stemming from the reading power will be eliminated in the distance vision power and vice versa, at no loss of intensity, when compared with the light intensity available from conventional polarizing sunglasses, i.e., essentially 50% of the incident light intensity will be available in each of the two foci. The physical appearance of sunglasses of such a design is not distinguishable from that of conventional polarizing sunglasses, such being cosmetically advantageous.

If the optic axes of two birefringent lenses are not at 90°, there will be, in general, four different powers because both the o- and e- powers of the first lens combine with the o- and e- powers of the second. In the lens system of FIG. 5, the two additional powers would be −0.51 and −0.47 diopters, i.e., the lens is practically trifocal.

Figure 7:
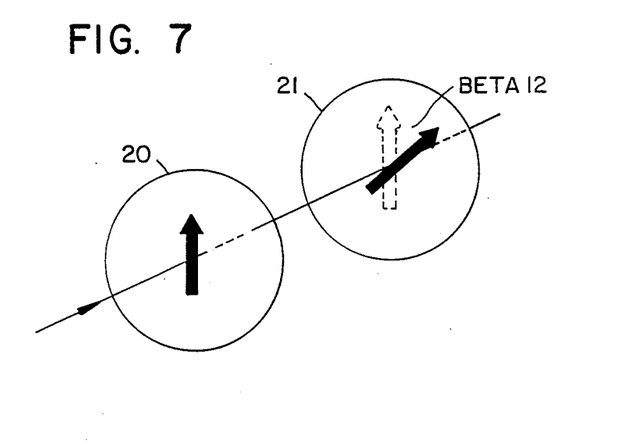
FIG. 7 is a schematic illustration of a birefringent lens up system made of two birefringent lens components exhibiting more than two simultaneous powers.

A birefringent lens system incorporating two birefringent lens components, 20 and 21, in which the angle between the optic axes is other than 90° is shown in FIG. 7. In general, the four powers of a lens system incorporating two birefringent components are given by:

$$D_{1o} + D_{2o} = D_a \quad (8a)$$

$$D_{1o} + D_{2e} = D_b \quad (8b)$$

$$D_{1e} + D_{2o} = D_c \quad (8c)$$

$$D_{1e} + D_{2e} = D_d \quad (8d)$$

wherein $D_{1o}$ is the power of the first lens for the o-rays, $D_{1e}$ the power of the first lens for the e-rays, and so on, and $D_a$, $D_b$, $D_c$ and $D_d$ are the resulting powers of the combinations, wherein the two lenses are in contact.

To a good approximation, the power of a lens is given by (see J. Strong, loc. cit., p. 319):

$$D = (n-1) \times S \quad (9)$$

wherein D is the power, n is the index of refraction and S is the so-called "shape factor" of the lens. Equation (9) can also be applied for the case of a birefringent lens of non-perfect geometry (e.g., FIGS. 3A, 4 and 5). In view of equation (9), the powers $D_{1o}$ and $D_{1e}$ of the first lens for the o- and e-rays are given by:

$$D_{1o} = (n_{1o} - 1) \times S_1 \quad (10a)$$

$$D_{1e} = (n_{1e} - 1) \times S_1 \quad (10b)$$

$$\text{or } D_{1e} = m_1 \times D_{1o} \quad (10c)$$

where $$m_1 = \frac{n_{1e} - 1}{n_{1o} - 1} \quad (5')$$

and wherein $n_{1e}$ and $n_{1o}$ are the indices of refraction of the first lens for the e- and o-rays, respectively. Analogous relations apply for the second lens.

By way of a specific embodiment, a lens consisting of two birefringent lens components and fabricated from the same birefringent medium is discussed. In view of equs. (5'), (10) and (8), the four powers of the lens system according to this embodiment are given by:

$$D_{1o} + D_{2o} = D_a \quad (11a)$$

$$D_{1o} + m \times D_{2o} = D_b \quad (11b)$$

$$m \times D_{1o} + D_{2o} = D_c \quad (11c)$$

$$m \times D_{1o} + m \times D_{2o} = D_d \quad (11d)$$

This set of equations is redundant: therefore, it is not possible to preselect the four powers independently one from the others. Equation (11) allows only the preselection of two of the resulting four powers. This is true also for the case of two birefringent lens components fabricated from different birefringent media.

If a lens system according to FIG. 7 should be trifocal, two of the four powers must be equal. As is evident from equation (11), only the two possibilities:

$$D_a = D_d \quad (12)$$

or $$D_b = D_c \quad (13)$$

exist.

In the case where $D_a = D_d$, then $D_{1o} = -D_{2o}$ and consequently $D_a = D_d = 0$. The three powers of this lens system are then:

$$D_b = D_{1o} \times (1 - m) \quad (14)$$

$$D_a = D_d = 0 \quad (15)$$

$$D_c = -D_{1o} \times (1 - m) \quad (16)$$

i.e., they are equally spaced. The constant interval between the three powers can be chosen freely, i.e., two of the three powers can be preselected. The choice of the interval determines the value $D_{1o}$. At any given choice of one lens surface, then $D_{1o}$ determines the other lens surfaces if the two lenses possess common or complementary opposed surfaces.

The case $D_b = D_c$ results in $D_{1o} = D_{2o}$, and the three powers will be given by $$D_a = 2 \times D_{1o} \quad (17)$$

$$D_b = D_c = (m+1) \times D_{1o} \quad (18)$$

$$D_d = 2 \times m \times D_{1o} \quad (19)$$

As can be seen from equations (17) through (19), a value for one of the three powers also determines the other two powers; thus, for this particular case, the possibility to preselect two powers independently one of the other does not exist.

From the preceding discussion, it is evident that through the addition of an isotropic lens, the set of powers can be shifted to a desired set of values, without, of course, altering the differences between the individual powers.

Figure 8:
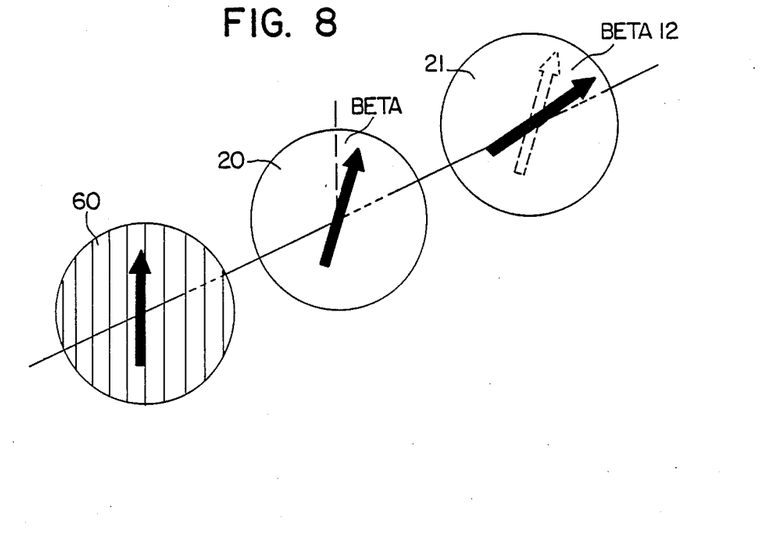
FIG. 8 is a schematic illustration of the lens system of FIG. 7 in combination with a polarizing means; and, FIGS. 9A and 9B are schematic illustrations, respectively, of front and side views of a spectacle lens incorporating a birefringent lens system in accordance with this invention.

If in a lens system incorporating two birefringent lenses the birefringent lenses are provided with a degree of freedom for rotation about the lens axis, the lens system acts either as a quadra- or bifocal lens when unpolarized light is used, or as a quadra-, bi- or monofocal lens when polarized light is incident on the lens system. FIG. 8 schematically illustrates such a lens system which incorporates a polarizer 60 and two birefringent lens components 20 and 21. As indicated, supra, only two of the four available powers can be predetermined independently if two birefringent lens components and no isotropic lens components are integrated in the system. If, by way of example, one of the two birefringent lens components is combined with another isotropic or birefringent lens component, the combined lens component exhibits two independently selectable powers $D_1$ and $D_2$. Consequently, the four resulting powers are now given by:

$$D_1 + D_{2o} = D_a \quad (20a)$$

$$D_1 + m \times D_{2o} = D_b \quad (20b)$$

$$D_2 + D_{2o} = D_c \quad (20c)$$

$$D_2 + m \times D_{2o} = D_d \quad (20d)$$

It can be concluded from the set of equation (20) that any three of the four powers can be given preselected values, leaving only one, the fourth power, as a function of the preselected three powers.

Generalizing the above results, the following can be concluded:

(1) A single birefringent lens of given medium exhibits two different simultaneous powers; only one of the two powers can be given a preselected value, the second power being a function of this predetermined value.

(2) A lens system consisting of a birefringent lens component and an isotropic or another birefringent lens component exhibits two powers each of which can be preselected in complete independence one of the other.

(3) A lens system consisting of two birefringent lenses exhibits four powers in general; two of the four powers can be preselected independently, the remaining two powers being functions of the two selected powers.

(4) If the two birefringent lenses are combined with an isotropic or another birefringent lens component, three of the four available powers can be preselected, only the fourth being a function of the three preselected ones.

(5) It can be shown that in a lens system incorporating three birefringent lenses, only three of the total eight resultant powers can be predetermined independently.

(6) If the three birefringent lenses are combined with an isotropic or another birefringent lens component, four of the eight resulting powers can be given arbitrarily preselected values.

In general, the number N of resulting powers of a lens system incorporating M birefringent lenses is given by (see, e.g., Eng. et al., loc. cit., supra):

$$N = 2^M \quad (21)$$

The number $N_{free}$ of powers to be selected in complete independence is $$N_{free} = M \quad (22)$$

If, in the system consisting of M birefringent lens components, at least one component is combined with an isotropic or another birefringent lens component, the number of resulting powers is again N but the number $N_{free}$ is given by $$N_{free} = M + 1 \quad (23)$$

The above relations apply for the case of M predetermined birefringent media. If there is a choice in the selection of the M birefringent media, it is possible that more than the $N_{free}$ powers can be given desired values.

Birefringent lenses and lens systems offer the possibility to attribute different intensities to different powers. In the discussion of intensity relations, it is to be noted first, that the amplitude of incident natural light is divided vectorially, i.e., the amplitudes $A_o$ and $A_e$ associated with the o- and e-waves, respectively, each exhibit a value $$A_o = A_e = \frac{A \times 2^{0.5}}{2} \quad (24)$$

wherein A is the amplitude of the incident light. It follows that 50% of the available intensity is directed to each of the two foci. Therefore, the relation between the intensities of the focused and the out-of-focus light is 1:1 in each of the two foci. This compares extremely favorably with other known simultaneous vision bifocal lens designs, supra.

Figure 6:
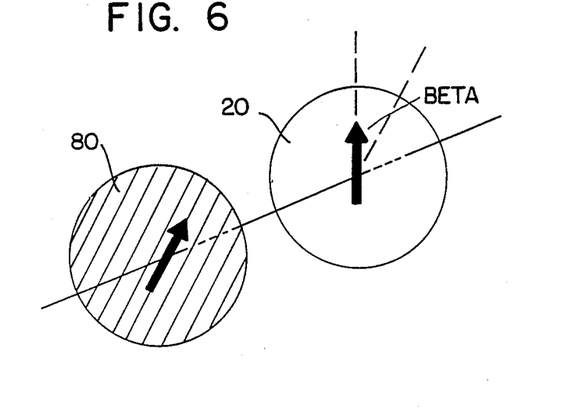
FIG. 6 is a schematic illustration of a birefringent lens system of this invention in combination with a polarizing means.

This ratio can be given any desired value if linearly polarized light is incident on a lens system incorporating at least one birefringent lens. FIG. 6 schematically illustrates a birefringent lens system in which the relative orientation of the optic axis of birefringent lens component 20 with respect to the plane of vibration of the incident polarized light is characterized by the angle beta. The polarized light is produced by a polarizing means 80. The intensities $I_o$ and $I_e$ associated with the o- and e-rays, respectively, are given by:

$$I_o = I_p \sin^2 \text{beta} \quad (25a)$$

$$I_e = I_p \cos^2 \text{beta} \quad (25b)$$

wherein $I_p$ is the intensity of the incident polarized light. In view of equation (25), it is clear that the ratio between $I_o$ and $I_e$ can be given any value by a proper selection of the angle beta. If a common polarizing filter is used for the production of polarized light, this will be achieved, as will be appreciated, with a loss of overall intensity. But in certain applications, it may be more important to reduce in one power the intensity of the out-of-focus light than to have higher, but equal, intensities associated with both powers. Furthermore, in some applications it is possible to use a high transmission polarizer, e.g., as disclosed in U.S. Pat. No. 3,552,985 in which case the overall available intensity is unaffected.

The above considerations apply to birefringent bifocal lens systems in general, i.e., for systems incorporating, e.g., two crossed birefringent lens components (FIG. 5) or a lens system incorporating one birefringent and one or more isotropic lens components (FIGS. 3A, 3B and 4).

The intensities associated with the four powers of a birefringent lens system according to FIG. 7 are given by:

$$I(OO) = (I/2) \times \cos^2 \text{beta}_{12} \quad (26a)$$

$$I(OE) = (I/2) \times \sin^2 \text{beta}_{12} \quad (26b)$$

$$I(EO) = (I/2) \times \sin^2 \text{beta}_{12} \quad (26c)$$

$$I(EE) = (I/2) \times \cos^2 \text{beta}_{12} \quad (26d)$$

where I(OO) is the intensity associated with the o-rays in the first and the o-rays in the second, birefringent lens, and so forth. I is the intensity of the incident unpolarized light and $\text{beta}_{12}$ is the angle between the optic axes of the two birefringent lens components. It is apparent from equation (26) that a certain degree of freedom exists in attributing intensities to the different powers. If, e.g., the lens system is made trifocal with equal intensities in all three powers, then for the case $D_{1o} = -D_{2o}$ supra. the angle $\text{beta}_{12}$ is determined by:

$$I(OO) + I(EE) = I(OE) = I(EO) \quad (27)$$

or $$\cos^2 \text{beta}_{12} = (\sin^2 \text{beta}_{12})/2 \quad (27')$$

which results in $$\text{beta}_{12} = 54.7° \quad (28)$$

For the other possible case, $D_{1o} = D_{2o}$, supra, the angle between the two optic axes must be $$beta_{12} = 35.3° \quad (29)$$

If a polarizing filter is used in front of a lens system incorporating two birefringent lens components and optionally one or more isotropic lens components, as illustrated in FIG. 8, the intensities associated with the four resultant powers are given by:

$$I(OO) = (I/2) \times \sin^2 beta \times \cos^2 beta_{12} \quad (30a)$$

$$I(OE) = (I/2) \times \sin^2 beta \times \sin^2 beta_{12} \quad (30b)$$

$$I(EO) = (I/2) \times \cos^2 beta \times \sin^2 beta_{12} \quad (30c)$$

$$I(EE) = (I/2) \times \cos^2 beta \times \cos^2 beta_{12} \quad (30d)$$

Equation (30) indicates that the lens system of FIG. 8 can be made mono-, bi-, or quadrafocal, if degrees of freedom for rotation of the birefringent lenses about the lens axis are provided.

B. Multifocal Birefringent Lens Systems Which Are Achromatic Or Which Exhibit A Predetermined Amount of Chromatic Aberration Multifocal lens systems in accordance with this invention which incorporate one or more birefringent and one or more isotropic lens components can also be achromatized to a varying degree. The following considerations for achromatizing lens systems are commensurate with the formalism, as e.g., presented by M. Herzberger in "Handbook of Physics", McGraw-Hill, 1967, p. 6–42. The Herzberger treatment of achromatism differs slightly from the more commonly employed theory, as e.g., presented in J. Strong loc. cit. p. 319 or M. Born, "Optik", Springer-Verlag, 1972, p.82. Furthermore, it is to be noted that the following description of achromatized birefringent lens systems herein requires that the individual components be "adjacent" to each other as this term is defined above but, unlike the non-achromatized lens systems described above, i.e., FIGS. 1, 3A, 3B and 4 to 9, they need not possess two opposed lens surfaces of identical or complementary curvature.

A lens system comprising one birefringent lens component and at least one isotropic lens component, either of perfect or non-perfect geometry, is achromatic in both preselected powers if the following set of equations can be solved (discussed is the more general case of one birefringent and two isotropic individual lenses), which case includes the perfect geometry embodiment):

$$D_{1,bl} + D_{2o,bl} + D_{3,bl} = D_{a,bl} \quad (31a)$$

$$D_{1,r} + D_{2o,r} + D_{3,r} = D_{a,r} \quad (31b)$$

$$D_{1,bl} + D_{2e,bl} + D_{3,bl} = D_{b,bl} \quad (31c)$$

$$D_{1,r} + D_{2e,r} + D_{3,r} = D_{b,r} \quad (31d)$$

with the conditions:

$$D_{a,bl} = D_{a,r} = D_a \quad (32)$$

and $$D_{b,bl} = D_{b,r} = D_b \quad (33)$$

In the set of equations (31) to (33) $D_{1,bl}$ refers to the power of isotropic lens "1" for blue ("bl") light $D_{2o,bl}$ to the power of birefringent lens "2" for the o-rays and for blue ("bl") light, $D_{3,r}$ to the power of isotropic lens 3 for red ("r") light, and so on.

It is noted that the subscripts "bl" and "r" are merely meant to refer to two different wavelengths and that the description which follows is not restricted to two particular wavelengths corresponding to blue and red light.

Use is made now, and in the following, of the fact that the shape factor S of a lens, supra, is to a close approximation given by:

$$S = \frac{D}{n-1} \quad (9')$$

where D is the power of a lens, and n is the index of refraction associated with this power. For the sake of simplicity, the value $n-1$ will be called n' henceforth, i.e.

$$n' = n - 1.$$

By way of example, the powers $D_{3,bl}$ and $D_{3,r}$ are interconnected therefore by the expression $$D_{3,r} = D_{3,bl} \times \frac{n'_{3,r}}{n'_{3,bl}} \quad (34)$$

If the lens system of equation (31) is to be achromatic in both powers, the following condition must be satisfied:

$$D_{2o,bl} - D_{2e,bl} = D_{2o,r} - D_{2e,r} \quad (35)$$

which results in the restriction $$n_{2o,bl} - n_{2e,bl} = n_{2o,r} - n_{2e,r} \quad (36)$$

The difference between the index of refraction for e- and for o-waves is called the "birefringence" of the medium. Consequently, a lens system incorporating one birefringent lens component and at least one isotropic lens component can be made achromatic in both preselected powers for both nonperfect and perfect geometry embodiments if the birefringence of the birefringent lens component is identical in two target wavelengths, e.g., "bl" and "r" as indicated above.

A lens system capable of producing two preselected powers and incorporating one birefringent lens and two isotropic lenses can in general be made achromatic in one of the two preselected powers. By way of example, a lens system is described in which the power corresponding to the e-rays is achromatic. Then the following set of equations must be solvable:

$$D_{1,bl} + D_{2e,bl} + D_{3,bl} = D_{a,bl} \quad (37a)$$

$$D_{1,r} + D_{2e,r} + D_{3,r} = D_{a,r} \quad (37b)$$

$$D_{1,bl} + D_{2o,bl} + D_{3,bl} = D_{b,bl} \quad (37c)$$

In view of equations (9') and (34), this set of equations transforms into:

$$\begin{bmatrix} 1 & \frac{n'_{2e,bl}}{n'_{2o,bl}} & 1 \\ \frac{n'_{1,r}}{n'_{1,bl}} & \frac{n'_{2e,r}}{n'_{2o,bl}} & 1 \\ 1 & 1 & 1 \end{bmatrix} \times \begin{bmatrix} D_{1,bl} \\ D_{2o,bl} \\ D_{3,bl} \end{bmatrix} = \begin{bmatrix} D_{a,bl} \\ D_{a,r} \\ D_{b,bl} \end{bmatrix} \quad (38)$$

Furthermore, for an achromatic lens, the condition $$D_{a,bl} = D_{a,r} \quad (39)$$

must hold. $D_{a,bl}$ and $D_{a,r}$ can be given preselected different values as well if the lens should exhibit a certain chromatic aberration in this power.

Equation (38) can be solved in general resulting in the specification of $D_{1,bl}$, $D_{2o,bl}$ and $D_{3,bl}$, and, in view of equation (34), of all other powers.

At a given power of a lens, one degree of freedom for the geometry of the lens remains. Consequently, three lenses in contact exhibit three such degrees of freedom, two in compound (i.e., sharing a common surface) with a third lens in contact exhibit two degrees of freedom and three lenses in compound still exhibit one degree of freedom for the geometry of such a lens system.

If it is desired that the lens system of equation (38) exhibit both achromatism in one of the preselected powers and also a perfect geometry, this can be achieved in various ways as follows:

(1) The birefringent lens component can be positioned in front, so that light is incident on it first, and the first surface of the birefringent lens is made a plane.

(2) The geometry of the lens system can be constrained by the condition $$D_1 = -D_{2e,fs} \quad (40)$$

where $D_{2e,fs}$ is the surface power of the first surface of the birefringent lens adjacent to the first isotropic lens and $D_1$ is the power of the first lens, both $D_1$ and $D_{2e,fs}$ corresponding to any visible wavelength.

(3) If the two isotropic lens components are positioned in front of the birefringent lens compound, the condition $$D_1 + D_3 = -D_{2e,fs} \quad (41)$$

must be satisfied, $D_3$ being the power of the remaining isotropic lens.

Strictly speaking, only a geometry according to (1) will be of the perfect geometry kind for both "bl" and "r" wavelengths and (2) and (3) produce perfect geometries for the wavelength chosen in equations (40) and (41) only. But, due to the usually modest wavelengths dependance of the refractive indices of isotropic and birefringent media, constraints (2) and (3) result in geometries which are essentially perfect.

Achromatizing birefringent lens systems in two preselected powers will now be described.

In the case of a lens system, incorporating two crossed birefringent lens components but no isotropic lens component, the following set of equations must be solvable:

$$D_{1o,bl} + D_{2e,bl} = D_{a,bl} \quad (42a)$$

$$D_{1o,r} + D_{2e,r} = D_{a,r} \quad (42b)$$

$$D_{1e,bl} + D_{2o,bl} = D_{b,bl} \quad (42c)$$

$$D_{1e,r} + D_{2o,r} = D_{b,r} \quad (42d)$$

with the achromatic conditions:

$$D_{a,bl} - D_{a,r} = D_{b,bl} - D_{b,r} = 0 \quad (43)$$

Equ. (42) and (43) can be solved provided the following condition holds:

$$(n_{1o,r} - n_{1e,r}) - (n_{2o,r} - n_{2e,r}) = (n_{1o,bl} - n_{1e,bl}) - (n_{2o,bl} - n_{2e,bl}) \quad (44)$$

Consequently, the difference between the birefringences of the two lenses must be equal for the two considered wavelengths. This, again, amounts to restriction on the birefringent media.

Finally, a lens system incorporating two crossed birefringent lens components and two isotropic lens components is described. If such a system is to be achromatic in both preselected powers, the following set of equations must be solvable:

$$D_{1,bl} + D_{2,bl} + D_{3e,bl} + D_{4,bl} = D_{a,bl} \quad (45a)$$

$$D_{1,r} + D_{2o,r} + D_{3e,r} + D_{4,r} = D_{a,r} \quad (45b)$$

$$D_{1,bl} + D_{2e,bl} + D_{3o,bl} + D_{4,bl} = D_{b,bl} \quad (45c)$$

$$D_{1,r} + D_{2e,r} + D_{3o,r} + D_{4,r} = D_{a,r} \quad (45d)$$

which transforms into $$\begin{bmatrix} 1 & 1 & \frac{n'_{3e,bl}}{n'_{3o,bl}} & 1 \\ \frac{n'_{1,r}}{n'_{1,bl}} & \frac{n'_{2o,r}}{n'_{2o,bl}} & \frac{n'_{3e,r}}{n'_{3o,bl}} & \frac{n'_{4,r}}{n'_{4,bl}} \\ 1 & \frac{n'_{2e,bl}}{n'_{2o,bl}} & 1 & 1 \\ \frac{n'_{1,r}}{n'_{1,bl}} & \frac{n'_{2e,r}}{n'_{2o,bl}} & \frac{n'_{3o,r}}{n'_{3o,bl}} & \frac{n'_{4,r}}{n'_{4,bl}} \end{bmatrix} \times \begin{bmatrix} D_{1,bl} \\ D_{2o,bl} \\ D_{3o,bl} \\ D_{4,bl} \end{bmatrix} = \begin{bmatrix} D_{a,bl} \\ D_{a,r} \\ D_{b,bl} \\ D_{b,r} \end{bmatrix} \quad (46)$$

If the two preselected powers are to be achromatic, equation (43) must also hold.

Equation (46) can be solved in general, but only for the case of two different birefringent media.

As already explained, supra, one degree of freedom for the geometry exists for a lens of given power. If the four lenses of equation (46) are in contact, but not in compound, there are at maximum four degrees of freedom for design purposes. These degrees of freedom can be used to produce lens systems of perfect geometry.

If, e.g., it is desired to assure that all e-rays are essentially at right angles with the optic axis in the first birefringent lens component, this lens component must be positioned behind an isotropic lens component, the isotropic lens component exhibiting a power $D_1$ which satisfies the condition $$D_1 = -D_{2e,fs}. \quad (47)$$

where $D_{2e,fs}$ is the front surface power of the first birefringent lens component for a visible wavelength.

If both the e-rays in the first birefringent lens component as well as the e-rays in the second birefringent lens component are to be perpendicular with the respective optic axes, then the front surfaces of the two birefringent lens components must be designated such that in addition to equation (47), the condition $$D_1 + D_{2o} = -D_{3e,fs} \tag{48}$$

must also be satisfied. $D_{3e,fs}$ is the front surface power of the second birefringent lens for e-rays and for a visible wavelength. Since only two degrees of freedom are required to satisfy equations (47) and (48) and since four degrees of freedom are available, a lens system can be provided in accordance with this invention which exhibits two independently preselected achromatic powers and also exhibits perfect geometries in both birefringent lens components.

It is to be noted that for lens components of high birefringence, the dependence of the index of refraction for the e-rays on the direction of the e-rays within the birefringent lens may be more important than the dependance of said index on the wavelength. Consequently, perfect geometry embodiments can be essential for the construction of achromatized multifocal birefringent lens systems.

If the two birefringent lens components are not crossed, i.e., if the angle between the two optic axes is other than 90° or 0°, this lens system exhibits four powers, supra, in general. Since the o-rays in a birefringent lens compare with ordinary light rays in an isotropic lens, the perfect geometry concept does not apply for the o-rays. Therefore the power associated with the o-rays in both the first and the second birefringent lens is achromatized in independence of whether the lens system satisfies the perfect geometry restriction for the e-rays or not. Consequently, the powers associated with the o- and the e-rays, with the o- and the e-rays and with the e- and o-rays in the first and second birefringent lens, respectively, satisfy the stringent achromatic and/or perfect geometry restrictions; only the power combination of the e-rays in the first and the e-rays in the second birefringent lens is not associated with a perfect geometry embodiment. Since three of the four resultant powers can be attributed preselected values, supra, it is advantageous to preselect the o-o-, the o-e- and the e-o powers.

In all foregoing considerations, it was assumed that the incident light consisted of parallel light rays. If any of the discussed lens systems is to be used for light of non-zero vergence, a collimator-lens which converts the non-zero vergence light into zero vergence light can be positioned in front of the lens system. This collimator lens itself can be a known or conventional achromat. The calculation of the then available preselectable powers of a system incorporating one or more additional isotropic lens components can be carried out on the basis of the described results for incident parallel light according to standard methods of optics. In doing so, it is generally possible to substitute any number j>2 of subsequent isotropic lens components by two isotropic lens components of powers $D_x$ and $D_y$, i.e., $$D_{1,bl} + D_{2,bl} + \ldots D_{j,bl} = D_{x,bl} + D_{y,bl} \tag{49a}$$

$$D_{1,r} + D_{2,r} + \ldots D_{j,r} = D_{x,r} + D_{y,r} \tag{49b}$$

can be solved in $D_x$ and $D_y$.

It is evident from the foregoing that the addition of polarizing means as well as the provision of a degree of freedom for rotation of the birefringent lens components and such polarizing means about the lens axis converts the lens systems of the present invention into variable achromatic power lens systems.

All considerations presented for non-achromatized lenses and lens systems, supra, apply also for achromatized lenses and lens systems.

Combinations of the present lens systems, either achromatized or non-achromatized, provide powerful optical devices and instruments. Since the sum of achromats is also achromatic, variable power devices are able to provide achromatic single or multiple powers if achromatic lens systems are used in combination with other achromatic lens systems. Different powers can be selected by a proper rotation of polarizing means and/or by the rotation of birefringent lens components or lens systems.

Furthermore, two or more birefringent lens systems, either achromatized or non-achromatized, can be combined into a system in which one or more of the lens systems exhibit also a degree of freedom for translation along the axis of the lens system. Such a combined system can be used as a variable power device, as is known from standard optics. Additional degrees of freedom for rotation of birefringent lens components and/or polarizing means can add additional degrees of freedom for the selection of desired powers.

These remarks are to be understood only as an indication of the vast field of possible applications of the lens systems according to the present invention. Such applications include, e.g., cameras, telescopes, microscopes, photocopiers, optical benches, optical devices for robots, etc.

Although illustrative embodiments of the present invention have been described herein with reference to the accompanying drawings, it is to be understood that the invention is not limited to these precise embodiments, and that various other changes and modifications may be effected therein by one skilled in the art without departing from the scope or spirit of the invention.

What is claimed is:

1. A multifocal non-achromatized birefringent lens system which comprises:
   (a) a first lens component which is a first birefringent lens possessing two positive or negative powers $Do_a$ and $De_a$ in which $Do_a$ is the value of the power of the lens associated with the ordinary rays of said lens and $De_a$ is the value of the power of the lens associated with the extraordinary rays of said lens, the ratio $Do_a/De_a$ being determined by the indices of refraction and the orientation of the crystal optic axis of the lens; and,
   (b) a second lens component adjacent to said first lens component, the curvatures of the opposed surfaces of the first and second lens components being substantially identical or complementary, said second lens component being selected from the group consisting of
      (i) a second birefringent lens possessing two different positive or negative powers $Do_b$ and $De_b$ in which $Do_b$ is the value of the power of the lens associated with the ordinary rays of said lens and $De_b$ is the value of the power of the lens associated with the extraordinary rays of said lens, the ratio $Do_b/De_b$ being determined by the indices of refraction and the orientation of the crystal optic axis of the lens, and (ii) an isotropic lens possessing a positive, negative, or zero power D, provided that in the case of the lens system comprising first birefringent lens (a) and second birefringent lens (b) (i), said first birefringent lens (a) and said second birefringent lens (b) (i) are shaped and positioned such that at least two out of the four resulting powers $D_{o_a}+D_{o_b}$, $D_{o_a}+D_{e_b}$, $D_{e_a}+D_{o_b}$ and $D_{e_a}+D_{e_b}$ of the lens systems are selectable independently from one another, and in the case of the lens system comprising first birefringent lens (a) and isotropic lens (b) (ii), said first birefringent lens (a) and said isotropic lens (b) (ii) are shaped and positioned such that both of the resulting powers $D_{o_a}+D$ and $D_{e_a}+D$ are selectable independently from one another, said lens system exhibiting no unwanted power or powers, and said lens system employed as a contact lens.

2. The lens system of claim 1 wherein any one surface of first lens component (a) or second lens component (b) is given a curvature in independence of said preselected arbitrary powers and in independence of the orientation of the extraordinary rays of first birefringent lens (a) relative to the crystal optic axis of lens (a).

3. The lens system of claim 1 wherein a first lens component (b) is positioned in front of lens component (a) and a second lens component (b) is positioned behind lens component (a), any one surface of lens component (a) or either of lens components (b) being given a curvature in independence of said preselected powers and all extraordinary rays of lens component (a) being perpendicular to the crystal optic axis of lens component (a).

4. The lens system of claim 1 wherein at least one birefringent lens is fabricated from a polymeric birefringent material.

5. The lens system of claim 1 possessing three or more independently selected powers.

6. The lens system of claim 1 further comprising at least one polarizer means other than a birefringent lens and/or at least one polarizing filter.

7. The lens system of claim 6 wherein the polarizer means is positioned in front of and/or between the lens components and the polarizing filter, where present, is positioned in front of and/or in between and/or behind the lens components.

8. The lens system of claim 6 wherein at least one of the polarizer means, the birefringent lens and the polarizing filter exhibits a degree of freedom for rotation about the lens system axis.

9. A bifocal, birefringent lens system having two powers $D_a$ and $D_b$ which comprises (a) a first lens component which is a birefringent lens possessing two positive or negative powers, one of which, $D_{2o,bl}$, is for ordinary rays of blue light, the other of which, $D_{2e,bl}$, is for extraordinary rays of blue light, (b) a second lens component which is an isotropic lens exhibiting a power, $D_{1,bl}$, for blue light, and (c) a third lens component which is an isotropic lens exhibiting a power, $D_{3,bl}$, for blue light, said system satisfying the following equation wherein:

$n'_{2e,bl} = n_{2e,bl} - 1$ with $n_{2e,bl}$ being the extraordinary index of refraction of lens component (a) for blue light, $n'_{2o,bl} = n_{2o,bl} - 1$ with $n_{2o,bl}$ being the ordinary index of refraction of lens component (a) for blue light, $n'_{2e,r} = n_{2e,r} - 1$ with $n_{2e,r}$ being the extraordinary index of refraction of lens component (a) for red light, $n'_{1,r} = n_{1,r} - 1$ with $n_{1,r}$ being the index of refraction of lens component (b) for red light, $n'_{1,bl} = n_{1,bl} - 1$ with $n_{1,bl}$ being the index of refraction of lens component (b) for blue light, $D_{a,bl}$ and $D_{a,r}$ are respective powers for blue and red light for said $D_a$ power, and $D_{b,bl}$ is power for blue light for said $D_b$ power, $$\begin{pmatrix} 1 & \frac{n'_{2e,bl}}{n'_{2o,bl}} & 1 \\ \frac{n'_{1,r}}{n'_{1,bl}} & \frac{n'_{2e,r}}{n'_{2o,bl}} & 1 \\ 1 & 1 & 1 \end{pmatrix} \times \begin{pmatrix} D_{1,bl} \\ D_{2o,bl} \\ D_{3,bl} \end{pmatrix} = \begin{pmatrix} D_{a,bl} \\ D_{a,r} \\ D_{b,bl} \end{pmatrix}$$

wherein $D_{a,bl}$, $D_{a,r}$ and $D_{b,bl}$ are preselected arbitrary values.

10. The lens system of claim 9, wherein the curvature of at least one lens component is given a value such that all extraordinary rays of lens component (a) are perpendicular to the crystal optic axis of said lens component, (a).

11. The lens component of claim 9, wherein the curvatures of at least two lens components are given values such that the extraordinary rays of at least one birefringent lens component are perpendicular with the crystal optic axis of said birefringent lens component.

12. The lens system of claim 9 exhibiting no unwanted power or powers.

13. The lens system of claim 9, further comprising at least one polarizing means other than a birefringent lens and/or at least one polarizing filter.

14. The lens system of claim 13, wherein at least one of the polarizing means, the birefringent lens and the polarizing filter exhibits a degree of freedom for rotation about the lens system axis.

15. The lens system of claim 13, wherein at least one of the polarizer means, the birefringent lens and the polarizing filter exhibits a degree of freedom for rotation about the lens system axis.

16. A multifocal, birefringent lens system exhibiting at least two powers $D_a$ and $D_b$, comprising (a) a first lens component which is a birefringent lens possessing two positive or negative powers, one of which, $D_{2o,bl}$, is for ordinary rays of blue light, the other of which, $D_{2e,bl}$, is for extraordinary rays of blue light, (b) a second lens component which is a birefringent lens possessing two positive or negative powers, one of which, $D_{3o,bl}$, is for ordinary rays of blue light, the other of which $D_{3e,bl}$, is for extraordinary rays of blue light, (c) a third lens component which is an isotropic lens exhibiting a power, $D_{1,bl}$, for blue light, and (d) a fourth lens component which is an isotropic lens exhibiting a power, $D_{4,bl}$, for blue light, said system satisfying the following equation wherein $n'_{2o,r} = n_{2o,r} - 1$ with $n_{2o,r}$ being the ordinary index of refraction of lens component (a) for red light, $n'_{2o,bl} = n_{2o,bl} - 1$ with $n_{2o,bl}$ being the ordinary index of refraction of lens component (a) for blue light, $n'_{2e,bl} = n_{2e,bl} - 1$ with $n_{2e,bl}$ being the extraordinary index of refraction of lens component (a) for blue light, $n'_{2e,r} = n_{2e,r} - 1$ with $n_{2e,r}$ being extraordinary index of refraction of lens component (a) for red light, $n'_{3e,bl} = n_{3e,bl} - 1$ with $n_{3e,bl}$ being the extraordinary index of refraction of lens component (b) for blue light, $n'_{3o,bl} = n_{3o,bl} - 1$ with $n_{3o,bl}$ being the ordinary index of refraction of lens, component (b) for blue light, $n'_{3e,r} = n_{3e,r} - 1$ with $n_{3e,r}$ being the extraordinary index of refraction of lens component (b) for red light, $n'_{3o,r} = n_{3o,r} - 1$ with $n_{3o,r}$ being the ordinary index of refraction of lens component (b) for red light, $n'_{1,r} = n_{1,r} - 1$ with $n_{1,r}$ being the index of refraction of lens component (c) for red light, $n'_{1,bl} = n_{1,bl} - 1$ with $n_{1,bl}$ being the index of refraction of lens component (c) for blue light, $n'_{4,r} = n_{4,r} - 1$ with $n_{4,r}$ being the index of refraction of lens component (d) for red light, $n'_{4,bl} = n_{4,bl} - 1$ with $n_{4,bl}$ being the index of refraction of lens component (d) for blue light, $D_{a,bl}$ and $D_{a,r}$ are respective powers for blue and red light for said $D_a$ power, and $D_{b,bl}$ and $D_{b,r}$ are respective powers for blue and red light for said $D_b$ power, $$\begin{pmatrix} 1 & 1 & \frac{n'_{3e,bl}}{n'_{3o,bl}} & 1 \\ \frac{n'_{1,r}}{n'_{1,bl}} & \frac{n'_{2o,r}}{n'_{2o,bl}} & \frac{n'_{3e,r}}{n'_{3o,bl}} & \frac{n'_{4,r}}{n'_{4,bl}} \\ 1 & \frac{n'_{2e,bl}}{n'_{2o,bl}} & 1 & 1 \\ \frac{n'_{1,r}}{n'_{1,bl}} & \frac{n'_{2e,r}}{n'_{2o,bl}} & \frac{n'_{3o,r}}{n'_{3o,bl}} & \frac{n'_{4,r}}{n'_{4,bl}} \end{pmatrix} \times \begin{pmatrix} D_{1,bl} \\ D_{2o,bl} \\ D_{3o,bl} \\ D_{4,bl} \end{pmatrix} = \begin{pmatrix} D_{a,bl} \\ D_{a,r} \\ D_{b,bl} \\ D_{b,r} \end{pmatrix}$$

wherein $D_{a,bl}$, $D_{a,r}$, $D_{b,bl}$ and $D_{b,r}$ are preselected arbitrary values.

17. The lens system of claim 16, wherein the curvature of at least one lens component is given a value such that all extraordinary rays of lens component (a) are perpendicular to the crystal optic axis of said lens component (a).

18. The lens component of claim 16, wherein the curvature of at least two lens components are given values such that the extraordinary rays of at least one birefringent lens component are perpendicular with the crystal optic axis of said birefringent lens component.

19. The lens system of claim 16 exhibiting no unwanted power or powers.

20. The lens system of claim 16, further comprising at least one polarizer means other than a birefringent lens and/or at least one polarizing filter.

* * * * *